United States Patent
Yoshikawa et al.

(10) Patent No.: US 10,846,850 B2
(45) Date of Patent: Nov. 24, 2020

(54) MORBIDITY DIAGNOSIS SUPPORT SYSTEM, MORBIDITY DIAGNOSIS DATA-GENERATING SYSTEM, AND MORBIDITY DIAGNOSIS SUPPORT METHOD

(71) Applicant: THE DOSHISHA, Kyoto (JP)

(72) Inventors: Kenichi Yoshikawa, Kyoto (JP); Masaya Ikegawa, Kyoto (JP); Takahiro Kenmotsu, Nara (JP); Nobuto Kakuda, Kyoto (JP); Takuto Nakamura, Tokyo (JP); Keisuke Danno, Shiga (JP); Natsumi Okoso, Osaka (JP); Naohiko Nakamura, Kyoto (JP); Kohta Iguchi, Kyoto (JP); Etsuro Hatano, Nara (JP); Shinji Uemoto, Shiga (JP)

(73) Assignee: THE DOSHISHA, Kyoto (JP)

(*) Notice: Subject to any disclaimer, the term of this patent is extended or adjusted under 35 U.S.C. 154(b) by 92 days.

(21) Appl. No.: 16/319,836

(22) PCT Filed: Jul. 24, 2017

(86) PCT No.: PCT/JP2017/026690
§ 371 (c)(1),
(2) Date: Jan. 23, 2019

(87) PCT Pub. No.: WO2018/021240
PCT Pub. Date: Feb. 1, 2018

(65) Prior Publication Data
US 2019/0172203 A1    Jun. 6, 2019

(30) Foreign Application Priority Data
Jul. 25, 2016 (JP) ................... 2016-145435

(51) Int. Cl.
*G06T 7/00* (2017.01)
*G01N 33/48* (2006.01)
(Continued)

(52) U.S. Cl.
CPC ......... *G06T 7/0012* (2013.01); *G01N 1/2813* (2013.01); *G01N 33/48* (2013.01);
(Continued)

(58) Field of Classification Search
CPC ......... G06T 7/0012; G06T 2207/30024; G06T 2207/10056; G06T 2207/10088;
(Continued)

(56) References Cited

U.S. PATENT DOCUMENTS

2010/0082019 A1* 4/2010 Neev ............... C12N 13/00 606/9
2012/0070606 A1* 3/2012 Villata ............ C08J 9/42 428/71
(Continued)

FOREIGN PATENT DOCUMENTS

| JP | 2005-021606 | 1/2005 |
| WO | 2013/077337 | 5/2013 |
| WO | WO 2016/087592 A1 | 6/2016 |

OTHER PUBLICATIONS

Official Communication issued in International Bureau of WIPO Patent Application No. PCT/JP2017/026690, dated Oct. 17, 2017.
(Continued)

*Primary Examiner* — Dung Hong
(74) *Attorney, Agent, or Firm* — Greenblum & Bernstein, P.L.C.

(57) ABSTRACT

Provided are a morbidity diagnosis support system, a morbidity diagnosis data-generating system, and a morbidity diagnosis support method that are capable of supporting a highly reliable morbidity diagnosis. A morbidity diagnosis
(Continued)

support system includes an extension device for extending a tissue section of cells, an image-photographing device for acquiring image data by image-photographing the tissue section, an image analysis device for analyzing the image data to calculate an index of morbidity based on a mode of cracks generated in the tissue section by the extension, and an output device for outputting the calculated index.

11 Claims, 10 Drawing Sheets

(51) Int. Cl.
    *G16H 50/20*     (2018.01)
    *G01N 1/28*     (2006.01)
    *G01N 33/483*     (2006.01)

(52) U.S. Cl.
    CPC ......... *G01N 33/4833* (2013.01); *G16H 50/20* (2018.01); *G01N 1/28* (2013.01); *G06T 2207/30024* (2013.01)

(58) Field of Classification Search
    CPC ... G06T 7/11; G01J 3/2823; G01J 2003/2826; G01J 2003/1269
    See application file for complete search history.

(56) References Cited

U.S. PATENT DOCUMENTS

| | | | |
|---|---|---|---|
| 2014/0255978 A1* | 9/2014 | Morimoto | G01N 1/31 435/30 |
| 2016/0058274 A1* | 3/2016 | Chiba | A61B 5/14546 600/328 |
| 2017/0053398 A1* | 2/2017 | Mahoor | G06K 9/4604 |
| 2017/0270666 A1* | 9/2017 | Barnes | G06T 7/12 |
| 2018/0204324 A1* | 7/2018 | Kawaguchi | G01N 33/483 |

OTHER PUBLICATIONS

European Search Report issued in corresponding European Patent Office Application No. 17834246.5, dated Dec. 4, 2019.

* cited by examiner

MORBIDITY DIAGNOSIS SUPPORT SYSTEM, MORBIDITY DIAGNOSIS DATA-GENERATING SYSTEM, AND MORBIDITY DIAGNOSIS SUPPORT METHOD

TECHNICAL FIELD

The present invention relates to a morbidity diagnosis support system, a morbidity diagnosis data-generating system, and a morbidity diagnosis support method that support morbidity diagnosis using tissue sections of cells.

BACKGROUND ART

As a method for diagnosing morbidity of a subject to be diagnosed, it is a standard method to observe tissue sections of cells obtained from the subject with an optical microscope and to diagnose based on morphology of cells at a micro level. However, even in the case of observing tissue sections with a microscope, there are many cases where it is difficult to discriminate, for example, whether a tumor contained in the tissue section is benign or malignant. Therefore, a morbidity diagnosis support system and a morbidity diagnosis support method that support morbidity diagnosis have been required.

Patent Document 1 describes a diagnosis support device consisting of X-ray equipment. This diagnosis support device calculates frequency coefficients by subjecting an image photographed by X-ray equipment to two-dimensional discrete wavelet transform processing, and calculates and displays an objective index of a tumor from an average value of frequency coefficients calculated for each frequency band.

PRIOR ART DOCUMENT

Patent Document

Patent Document 1: JP-A-2005-21606

SUMMARY OF THE INVENTION

Problems to be Solved by the Invention

Incidentally, it is known that non-alcoholic steatohepatitis (NASH) progresses as a preliminary stage of occurrence of hepatocellular carcinoma (HCC), which is a primary liver cancer, and it is known to have simple steatosis as a preliminary stage of onset of non-alcoholic steatohepatitis.

However, when diagnosing morbidity based on the index calculated by the method of Patent Document 1, for example, there is a risk that it is not possible to finely discriminate a plurality of morbidity until the above hepatocellular carcinoma occurs. Therefore, there is a problem that it is not possible to support a highly reliable morbidity diagnosis.

The present invention has been made in view of the above circumstances, and it is an object to provide a morbidity diagnosis support system, a morbidity diagnosis data-generating system, and a morbidity diagnosis support method that are capable of supporting a highly reliable morbidity diagnosis.

Means for Solving the Problems

In order to solve the above problems, the present invention includes an extension device for extending a tissue section of cells, an image-photographing device for acquiring image data by image-photographing the tissue section, an image analysis device for analyzing the image data to calculate an index of morbidity based on a mode of cracks generated in the tissue section by the extension, and an output device for outputting the calculated index.

In addition, in the above configuration, the extension device extends the tissue section by, for example, clipping the stretchable sheet provided with the tissue section, and stretching the stretchable sheet.

Also, in the above configuration, the stretchable sheet is formed of, for example, polyurethane gel.

Moreover, in the above configuration, the image analysis device calculates, for example, an area of cells contained in the tissue section and an area of cracked part generated in the tissue section, and calculates the index based on the area of cells and the area of cracked part.

Further, in the above configuration, the image analysis device calculates, for example, an area of cracked part generated in the tissue section and a length of cracked part, and calculates the index based on the area and length of cracked part.

Furthermore, in the above configuration, the image analysis device converts, for example, at least a part of an image photographed by the image-photographing device into a spatial frequency domain, and calculates the index based on a frequency distribution obtained as a result of conversion into the spatial frequency domain.

Also, in the above configuration, the image analysis device calculates a spatial correlation coefficient representing a feature of a geometric shape of a crack based on a shape of the crack on an image photographed by the image-photographing device, and calculates the index based on the spatial correlation coefficient.

In addition, in order to solve the above problems, the present invention includes an extension device for extending a tissue section of cells and an image-photographing device for acquiring image data as analysis data by image-photographing the tissue section, in a morbidity diagnosis data-generating system for generating the analysis data for supporting morbidity diagnosis.

Moreover, in order to solve the above problems, the present invention includes a tissue section extension step of extending a tissue section of cells, an image data acquisition step of acquiring image data of the tissue section by an image-photographing device, an index calculation step of calculating an index of morbidity based on a mode of cracks generated in the tissue section by the extension, by allowing an image analysis device to analyze the image data, and an index output step of outputting the index by an output device.

Further, in the above configuration, for example, a prepared slide creation step of creating a prepared slide by providing the tissue section on a stretchable sheet is further included, and the tissue section is extended by stretching the stretchable sheet in the tissue section extension step.

Furthermore, in the above configuration, for example, the tissue section is stained in the prepared slide creation step.

Also, in the above configuration, for example, a polyurethane gel sheet is used as the stretchable sheet in the prepared slide creation step.

Effect of the Invention

According to the present invention, it is possible to provide a morbidity diagnosis support system, a morbidity

BRIEF DESCRIPTION OF THE DRAWINGS

FIGS. 3(A) to 3(D) are micrographs obtained by image-photographing tissue sections of mouse hepatocytes, wherein FIG. 3(A), shows a hepatocyte in a normal state, FIG. 3(B) shows simple steatosis, FIG. 3(C) shows non-alcoholic steatosis, and FIG. 3(D) shows hepatocellular carcinoma.

MODE FOR CARRYING OUT THE INVENTION

Figure 1:
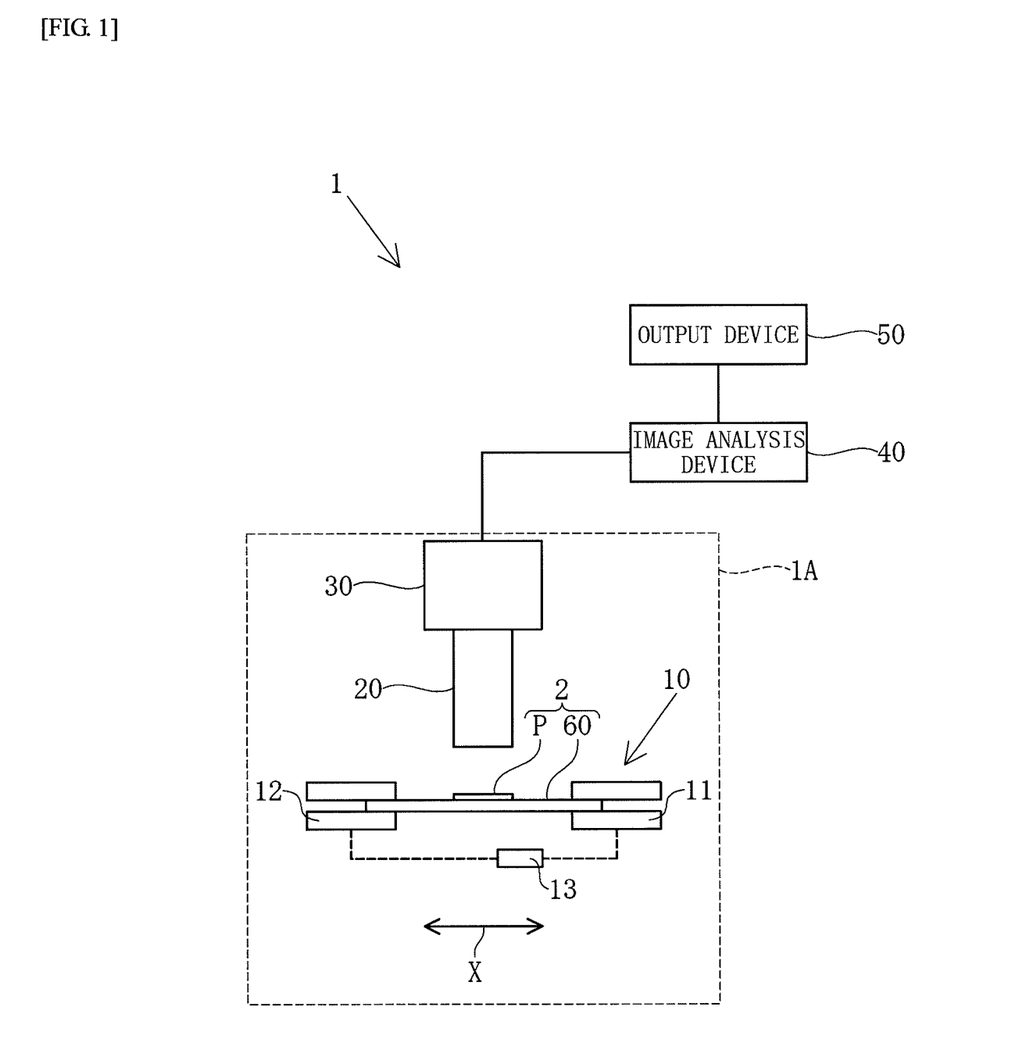
FIG. 1 is a schematic configuration diagram of a morbidity diagnosis support system according to an embodiment of the present invention.

Hereinafter, an embodiment of the present invention will be described with reference to the accompanying drawings. FIG. 1 shows a schematic configuration of a morbidity diagnosis support system 1 according to the present invention. The morbidity diagnosis support system 1 includes a morbidity diagnosis data-generating system 1A.

As shown in FIG. 1, the morbidity diagnosis support system 1 supports morbidity diagnosis by using a prepared slide 2 containing a tissue section P of cells. The morbidity diagnosis support system 1 includes an extension device 10, a microscope 20, an image-photographing device 30, an image analysis device 40, and an output device 50. The prepared slide 2 is constituted by the tissue section P and a stretchable sheet 60 on which the tissue section P is placed.

The extension device 10 is constituted by a tension device equipped with an actuator. The extension device 10 extends the tissue section P by clipping the stretchable sheet 60 provided with the tissue section P and stretching the stretchable sheet 60 in surface direction X (extension direction) of the stretchable sheet 60. The extension device 10 is constituted by a first fixing portion 11 to which one end of the stretchable sheet 60 is fixed, a second fixing portion 12 to which the other end of the stretchable sheet 60 is fixed, and a linear actuator 13 for varying an interval between the first fixing portion 11 and the second fixing portion 12. The extension device 10 extends the stretchable sheet 60 and the tissue section P by increasing the interval between the first fixing portion 11 and the second fixing portion 12 by the linear actuator 13. Also, after extension of the tissue section P, the extension device 10 contracts the stretchable sheet 60 and the tissue section P by reducing the interval between the first fixing portion 11 and the second fixing portion 12 by the linear actuator 13. As the linear actuator 13, BioMetal Helix can be adopted. The linear actuator 13 constituted by BioMetal Helix can extend/contract the stretchable sheet 60 and the tissue section P by turning on/off the current supply to the BioMetal Helix.

The microscope 20 is constituted by an optical microscope, and the image-photographing device 30 is constituted by a digital camera for microscope. The image-photographing device 30 image-photographs the tissue section P through the microscope 20. The image-photographing device 30 includes an imaging element which is a photoelectric conversion element, and acquires image data of the tissue section P by image-photographing the tissue section P with the imaging element.

The morbidity diagnosis data-generating system 1A is constituted by the extension device 10, the microscope 20 and the image-photographing device 30 described above, and generates analysis data for supporting morbidity diagnosis. That is, the image-photographing device 30 acquires image data as the analysis data by image-photographing the tissue section P. The morbidity diagnosis data-generating system 1A provides the image analysis device 40 with the analysis data generated by the image-photographing device 30.

The image analysis device 40 is constituted by a personal computer which is a personal general purpose computer. The image analysis device 40 acquires the image data of the tissue section P from the image-photographing device 30 and analyzes the image data to calculate an index of morbidity based on the mode of cracks generated in the tissue section P by the extension. Specifically, the image analysis device 40 calculates an index of morbidity by performing at least one of the following (A) to (D).

(A) Calculate area C of cells contained in the tissue section P and area S of cracked part generated in the tissue section P, and calculate an index of morbidity based on the area C of cells and the area S of cracked part.

(B) Calculate the area S of cracked part generated in the tissue section P and a length L of cracked part, and calculate an index of morbidity based on the area S and length L of cracked part.

(C) Convert at least a part of an image photographed by the image-photographing device 30 into a spatial frequency domain, and calculate an index of morbidity based on a frequency distribution obtained as a result of conversion into the spatial frequency domain.

(D) Calculate a spatial correlation coefficient representing a feature of a geometric shape of a crack based on a shape of the crack on an image photographed by the image-photographing device 30, and calculate an index of morbidity based on the spatial correlation coefficient.

The output device 50 is constituted by a display visually presenting the index calculated by the image analysis device 40. Doctors can diagnose morbidity according to the mode of cracks of the tissue section P with reference to the index of morbidity outputted from the output device 50.

The stretchable sheet 60 is made of polyurethane gel which is a transparent and stretchable resin material. The stretchable sheet 60 has a self-adsorption property, and the tissue section P is placed on the stretchable sheet 60 so that the tissue section P can be stretchable together with the stretchable sheet 60.

Figure 2:
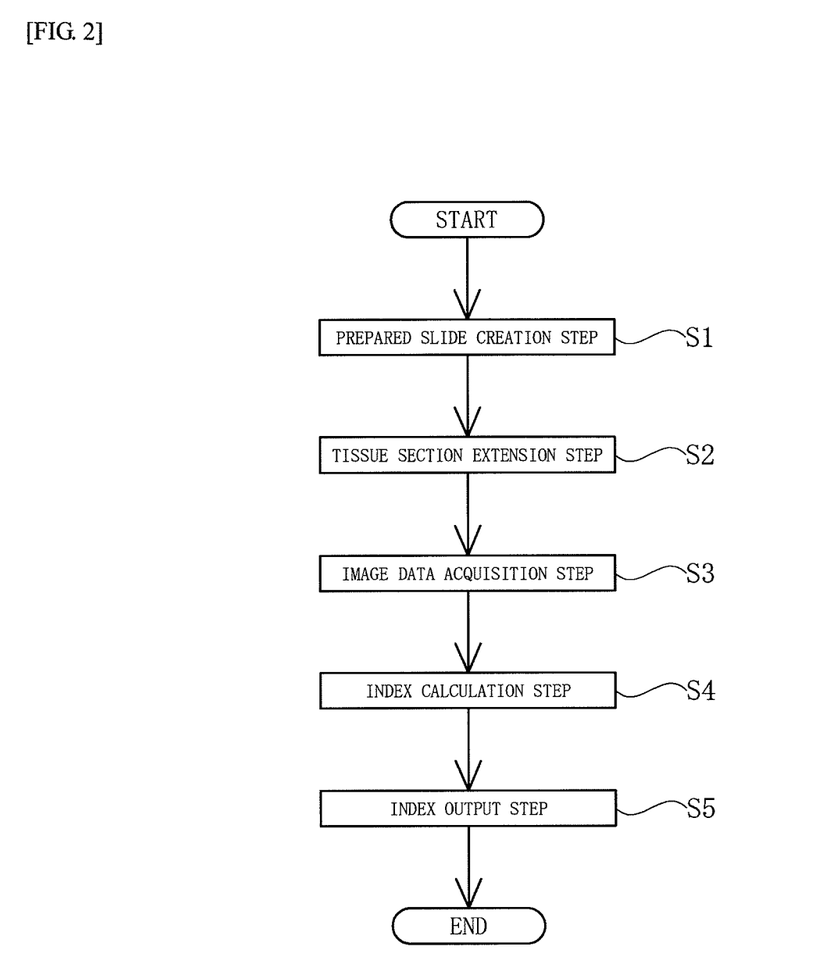
FIG. 2 is a flowchart showing a flow of a morbidity diagnosis support method according to the same embodiment.

With reference to FIG. 2, a flow of the morbidity diagnosis support method will be described.

As shown in FIG. 2, the morbidity diagnosis support method sequentially passes through a prepared slide creation step S1, a tissue section extension step S2, an image data acquisition step S3, an index calculation step S4, and an index output step S5 to support morbidity diagnosis.

In the prepared slide creation step S1, a tissue section P is provided on a stretchable sheet 60 which is a polyurethane gel sheet, and the tissue section P is stained to prepare a prepared slide 2. Next, in the tissue section extension step S2, by allowing the extension device 10 to stretch the stretchable sheet 60, the tissue section P is extended together with the stretchable sheet 60 so as to elastically deform. The extended stretchable sheet 60 and tissue section P contract after the tissue section extension step S2.

Subsequently, in the image data acquisition step S3, the image data of the tissue section P is acquired with the image-photographing device 30 by image-photographing the stretched tissue section P by use of the image-photographing device 30. Next, in the index calculation step S4, an index of morbidity based on the mode of cracks generated in the tissue section P by the extension is calculated, by allowing the image analysis device 40 to analyze the image data acquired in the step S3.

Then, in the index output step S5, the index calculated in the step S4 is outputted by the output device 50. Doctors can diagnose morbidity according to the mode of cracks of the tissue section P with reference to the index outputted in the step S5. As described above, the morbidity diagnosis support method according to the present embodiment supports morbidity diagnosis by a doctor.

According to the present embodiment, the following effects can be obtained.

(1) The morbidity diagnosis support system 1 includes an extension device 10 for extending a tissue section P, an image-photographing device 30 for acquiring image data by image-photographing the tissue section P, and an image analysis device 40 for analyzing the image data to calculate an index of morbidity based on the mode of cracks generated in the tissue section P by the extension, and an output device 50 for outputting the calculated index. According to this configuration, since the cracks generated in the tissue section P can be made conspicuous by extending the tissue section P, it becomes possible to distinguish the index of morbidity based on the mode of cracks according to a plurality of morbidity. Therefore, it is possible to accurately discriminate a plurality of morbidity based on the calculated and outputted indices, and it is possible to support a highly reliable morbidity diagnosis.

(2) The extension device 10 extends the tissue section P by clipping the stretchable sheet 60 provided with the tissue section P, and stretching the stretchable sheet 60. According to this configuration, it is possible to extend the tissue section P without directly stretching the tissue section P.

(3) The stretchable sheet 60 is formed of polyurethane gel. According to this configuration, it can be configured so that the tissue section P is stretched together with the stretchable sheet 60 merely by placing the tissue section P on the stretchable sheet 60.

(4) The morbidity diagnosis data-generating system 1A includes an extension device 10 for extending the tissue section P and an image-photographing device 30 for acquiring image data as analysis data by image-photographing the tissue section P. According to this configuration, since the cracks generated in the tissue section P can be made conspicuous by extending the tissue section P, it is possible for the image analysis device 40 to calculate indices that can be distinguished according to a plurality of morbidity based on the image data, by providing the image data of the tissue section P to the image analysis device 40. Therefore, it is possible to accurately discriminate a plurality of morbidity based on the image data of the extended tissue section P, and it is possible to support a highly reliable morbidity diagnosis.

(5) The morbidity diagnosis support method includes a step S2 of extending the tissue section P of cells, a step S3 of acquiring image data of the tissue section P by the image-photographing device 30, a step S4 of calculating an index of morbidity based on the mode of cracks generated in the tissue section P by the extension, by allowing the image analysis device 40 to analyze the image data, and a step S5 of outputting the calculated index by the output device 50. According to this configuration, the same effect as in the above (1) is exerted.

(6) The morbidity diagnosis support method includes a step S1 of creating a prepared slide 2 by providing the tissue section P on the stretchable sheet 60, and in the step S2, the tissue section P is extended by stretching the stretchable sheet 60. According to this configuration, the same effect as in the above (2) is exerted.

(7) In the morbidity diagnosis support method, a polyurethane gel sheet is used as the stretchable sheet 60 in the step S1. According to this configuration, the same effect as in the above (3) is exerted.

EXAMPLES

[Preparation of Tissue Section]

A liver of a mouse that develops liver cancer at 36 weeks by giving a high fat diet was frozen, and the frozen tissue was sliced with a tissue slicer to prepare a tissue section P with a thickness of 0.02 mm. As the tissue section P, a tissue section P1 obtained from a liver of a mouse before giving a high fat diet, a tissue section P2 obtained from a liver of a mouse given a high fat diet for 12 weeks, a tissue section P3 obtained from a liver of a mouse given a high fat diet for 24 weeks, and a tissue section P4 obtained from a liver of a mouse given a high fat diet for 36 weeks were prepared. The morbidity of the mouse given a high fat diet for 12 weeks is simple steatosis, and the morbidity of the mouse given a high fat diet for 24 weeks is non-alcoholic steatosis.

[Observation of Tissue Section]

Figure 3:
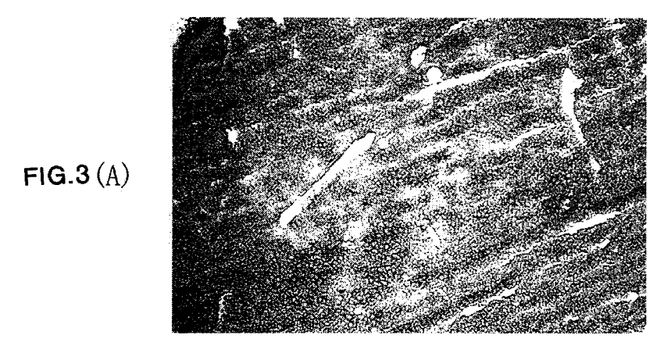

States in which the above-described tissue sections P1 to P4 are each attached to a glass slide, stained and observed with the microscope 20 are shown in FIG. 3. FIG. 3(A) is a micrograph of the tissue section P1, FIG. 3(B) is a micrograph of the tissue section P2, FIG. 3(C) is a micrograph of the tissue section P3, and FIG. 3(D) is a micrograph of the tissue section P4. As shown in FIGS. 3(A) to 3(D), it can be seen that some cracks occur in any of the tissue sections P1 to P4. In addition, it can be seen that a part of unstained spotted pattern becomes larger as morbidity worsens.

Example 1

Figure 4:
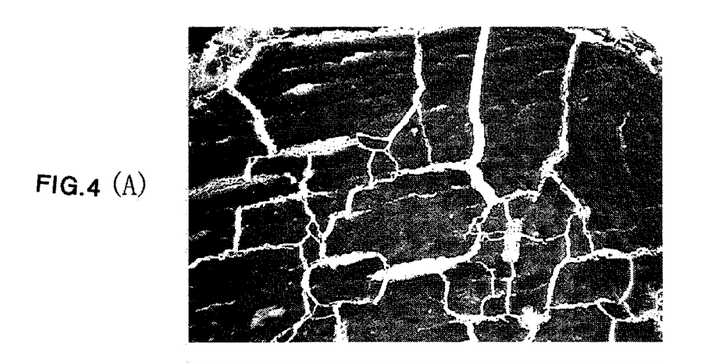
FIGS. 4(A) to 4(D) are micrographs obtained by image-photographing stretched tissue sections of mouse hepatocytes.

The tissue sections P1 to P4 obtained in the [Preparation of Tissue Section] are each attached to the stretchable sheet 60 made of a disc-shaped polyurethane gel with a thickness of 1 mm and a diameter of 5 cm and stained, thereby preparing four kinds of prepared slides 2 provided with the tissue sections P1 to P4. Each stretchable sheet 60 provided with the tissue sections P1 to P4 was extended in such a manner that the stretchable sheet 60 had a diameter of 7 cm in the extension direction which was one linear direction (that is, the stretchable sheet 60 was extended by 20 mm) by the extension device 10, and the tissue sections P1 to P4 on each stretchable sheet 60 contracted by elasticity were observed with the microscope 20. States of the stretched tissue sections P1 to P4 are shown in FIG. 4. FIG. 4(A) is a micrograph of the stretched tissue section P1, FIG. 4(B) is a micrograph of the stretched tissue section P2, FIG. 4(C) is a micrograph of the stretched tissue section P3, and FIG. 4(D) is a micrograph of the stretched tissue section P4. As shown in FIGS. 4(A) to 4(D), it can be seen that, cracks conspicuously appear in the stretched tissue sections P1 to P4, as compared to in the unextended tissue sections P1 to P4 shown in FIG. 3. Moreover, it can be seen that cracks become finer as morbidity worsens.

Figure 5:
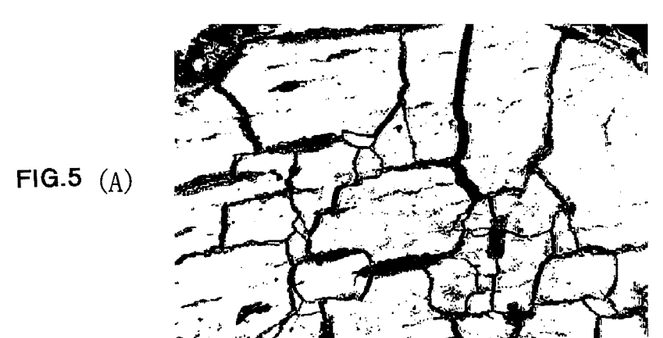
FIG. 5(A) is a binary image of FIG. 4(A)
FIG. 5(B) is a binary image of FIG. 4(B)
FIG. 5(C) is a binary image of FIG. 4(C)
FIG. 5(D) is a binary image of FIG. 4(D).

Next, image data of the tissue sections P1 to P4 were acquired by image-photographing the tissue sections P1 to P4 with the image-photographing device 30 through the microscope 20. The image data acquired by the image-photographing device 30 were inputted to the image analysis device 40, and binary processing is performed on the image data of the tissue sections P1 to P4 by the image analysis device 40 as a preprocessing of image analysis. Images of the tissue sections P1 to P4 subjected to binary processing are shown in FIG. 5. In the binary images of FIGS. 5(A) to 5(D), a black part is a cracked part.

Next, each image data of the tissue sections P1 to P4 was analyzed by the image analysis device 40, and the index of morbidity was calculated. The image analysis device 40 according to the present example calculated the index by performing the above (A). Specifically, the image analysis device 40 calculated the number of pixels of white part as the area C of cells, and calculated the number of pixels of black part as the area S of cracked part, in the binary images of the tissue sections P1 to P4. Then, the image analysis device 40 calculated the ratio [S/(C+S)] of the area S of cracked part to the sum of the area C of cells and the area S of cracked part as the index of morbidity. The ratios of the areas S calculated from each image data of the tissue sections P1 to P4 are shown in FIG. 6.

Figure 6:
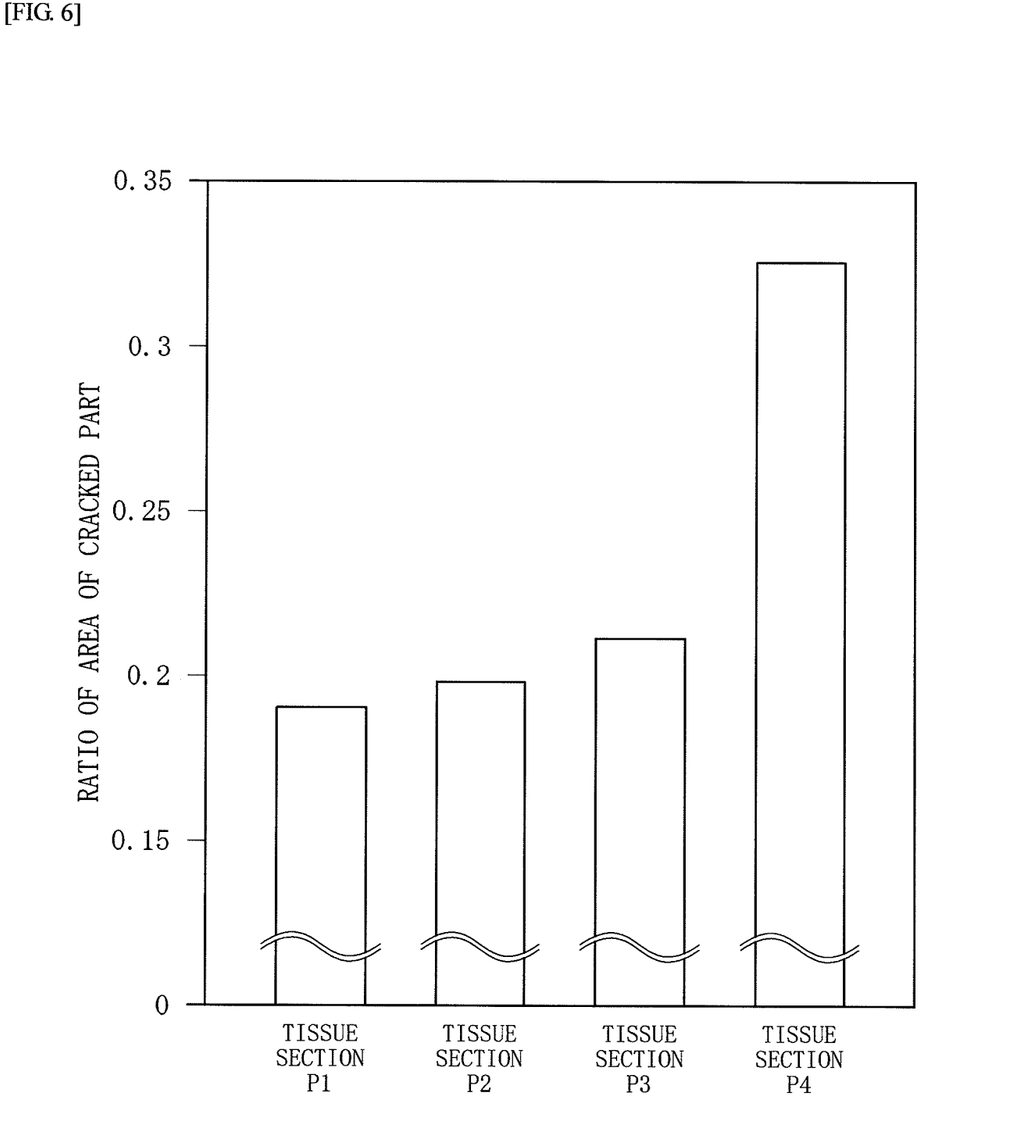
FIG. 6 is a graph showing indices of morbidity calculated in Example 1.

As shown in FIG. 6, it can be seen that the ratio of the area S of cracked part increases, particularly in the tissue of cancer as morbidity worsens. Moreover, it can be seen that the difference between the ratios of the areas S of the tissue sections P3 and P4 is larger than the difference between the ratios of the areas S of the tissue sections P2 and P3, and the difference is remarkable. Therefore, it is possible to easily discriminate between the morbidity of the tissue section P3 and the morbidity of the tissue section P4, by the ratio of the area S of cracked part.

Example 2

The present example is the same as Example 1, except for the method of calculating the index by the image analysis device 40. The image analysis device 40 according to the present example calculated the index by performing the above (B). Specifically, the image analysis device 40 calculates the number of pixels of black part as the area S of cracked part in the binary images of the tissue sections P1 to P4, and calculates the length of the boundary part between the black part and the white part extracted by contour extraction processing as the length L of cracked part. Then, the image analysis device 40 calculates γ calculated from the following equation (1), and calculates relative γ values by dividing γ calculated from each image data of the tissue sections P1 to P4 by γ calculated from the image data of the tissue section P1 as the indices of morbidity. That is, the relative γ value calculated from the image data of the tissue section P1 is 1, and the relative γ values calculated from the image data of the tissue sections P2 to P4 are values of the ratios of γ of the tissue sections P2 to P4 based on γ of the tissue section P1. The relative γ values calculated from each image data of the tissue sections P1 to P4 are shown in FIG. 7.

[Expression 1]

$$\gamma = \frac{L}{2\sqrt{\pi \cdot S}} - 1 \quad (1)$$

Figure 7:
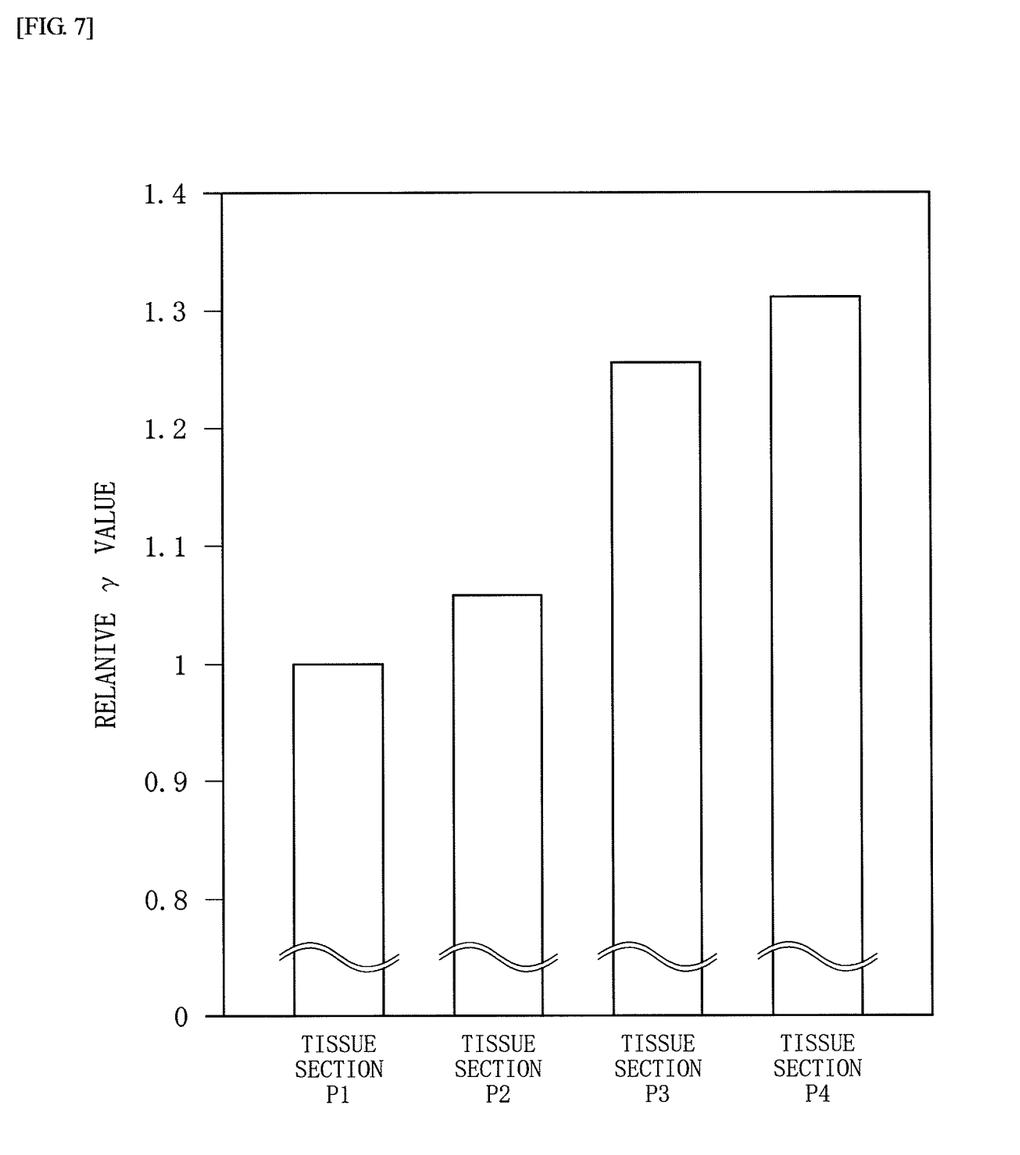
FIG. 7 is a graph showing indices of morbidity calculated in Example 2.

As shown in FIG. 7, it can be seen that the relative γ value increases as morbidity worsens. Moreover, it can be seen that the difference between the relative γ values of the tissue sections P2 and P3 is larger than the difference between the relative γ values of the tissue sections P1 and P2 and is also larger than the difference between the relative γ values of the tissue sections P3 and P4, and the difference is remarkable. Therefore, it is possible to easily discriminate between the morbidity of the tissue section P3 and the morbidity of the tissue section P4, by the relative γ value.

Example 3

The present example is the same as Example 1, except for the method of calculating the index by the image analysis device 40. The image analysis device 40 according to the present example calculated the index by performing the above (C). Specifically, the image analysis device 40 applies a fast Fourier transform (FFT) to the image data of the tissue sections P1 to P4 and converts the images of the tissue sections P1 to P4 into a spatial frequency domain. Then, based on the frequency distribution obtained as a result of conversion into the spatial frequency domain, the image analysis device 40 calculated the average value, the standard deviation, the maximum value, and the like of frequency components as indices of morbidity.

The frequency component of low spatial frequency (frequency component corresponding to long wavelength) obtained from the image of the tissue section P1 is relatively large, and the frequency component tends to be attenuated as morbidity worsens. That is, the frequency component of high spatial frequency (frequency component corresponding to short wavelength) tends to increase as morbidity worsens. Therefore, it is possible to easily discriminate morbidity by the average value, the standard deviation, the maximum value, and the like of frequency components.

Example 4

The present example is the same as Example 1, except for the method of calculating the index by the image analysis device 40. The image analysis device 40 according to the present example calculated the index by performing the above (D). Specifically, the image analysis device 40 calculated the ratio of the pixels of the same color as a reference pixel as the spatial correlation coefficient, in the binary images of the tissue sections P1 to P4.

Figure 8:
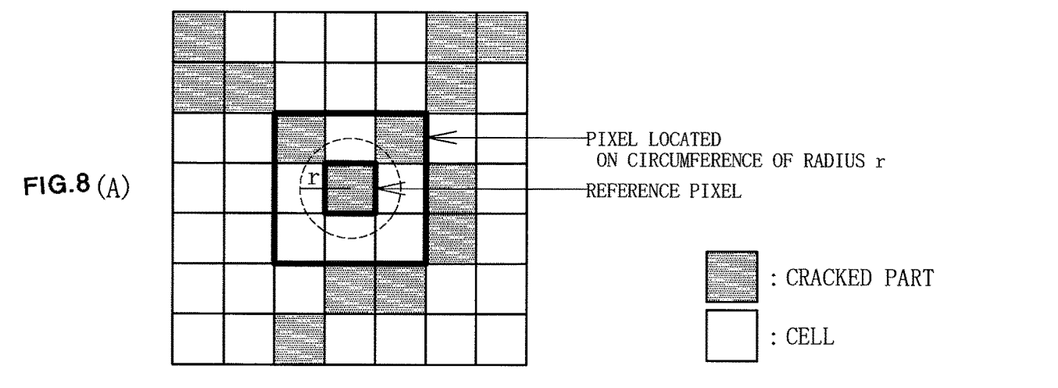
FIGS. 8(A) to 8(C) are schematic diagrams for describing a method of calculating a spatial correlation coefficient according to Example 4.

For example, as shown in FIG. 8(A), when the reference pixel is a pixel constituting a cracked part and radius r is 1 pixel, the ratio of the cracked part occupied in 8 pixels surrounded by a thick frame in the drawing is calculated as the spatial correlation coefficient. Also, for example, as shown in FIG. 8(B), when the reference pixel is a pixel constituting a cracked part and the radius r is 2 pixels, the ratio of the cracked part occupied in 16 pixels surrounded by a thick frame in the drawing is calculated as the spatial correlation coefficient. Moreover, for example, as shown in FIG. 8(C), when the reference pixel is a pixel constituting a cracked part and the radius r is 3 pixels, the ratio of the cracked part occupied in 24 pixels surrounded by a thick frame in the drawing is calculated as the spatial correlation coefficient. The spatial correlation coefficients calculated in FIGS. 8(A) to 8(C) are ⅖ (=¼), 6/16 (=⅜), and 5/24.

Next, the image analysis device 40 repeated calculation of spatial correlation coefficients by changing the reference pixel, and calculated the average spatial correlation coefficient based on a plurality of spatial correlation coefficients which differ depending on the position of the reference pixel. Further, the image analysis device 40 changed the size of the radius r and repeated the calculation of the average spatial correlation coefficient. That is, the image analysis device 40 calculated spatial correlation coefficients on a plurality of types of circumferences having different radii r included in the image. Then, based on the distribution of the average spatial correlation coefficients corresponding to a plurality of types of radii r, the image analysis device 40 calculated the average value, the standard deviation, the maximum value, and the like of the average spatial correlation coefficients as indices of morbidity.

The cracks generated in the tissue section P1 after extension have relatively many linear parts, and a spatial correlation function decreases at a part with a small radius r because of a jagged shape formed as morbidity worsens. Therefore, it is possible to easily discriminate morbidity by the average value, the standard deviation, the maximum value, and the like of the average spatial correlation coefficients.

Example 5

The present example is the same as Example 1, except for the method of calculating the index by the image analysis device 40. The image analysis device 40 according to the present example calculated the index by performing the above (D). Specifically, the image analysis device 40 calculated the ratio of black pixels occupied around white pixels in the binary images of the tissue sections P1 to P4 as a first spatial correlation coefficient, and further calculated coefficient and constant of an approximate expression according to the first spatial correlation coefficient as second spatial correlation coefficients.

Specifically, the image analysis device 40, using arbitrary white pixel as the reference pixel, calculated the ratio of the cracked part (black pixels) at a position apart from the reference pixel by pixels corresponding to radius R as the first spatial correlation coefficient, in the same manner as Example 4. Then, the image analysis device 40 repeated calculation of the first spatial correlation coefficients by changing the reference pixel, and calculated the average first spatial correlation coefficient E based on the first spatial correlation coefficients at 400 points. Further, the image analysis device 40 changed the size of the radius R and repeated calculation of the average first spatial correlation coefficients ε. Graphs of the average first spatial correlation coefficients ε calculated from each image data of the tissue sections P1 to P4 are shown in FIG. 9.

Figure 9:
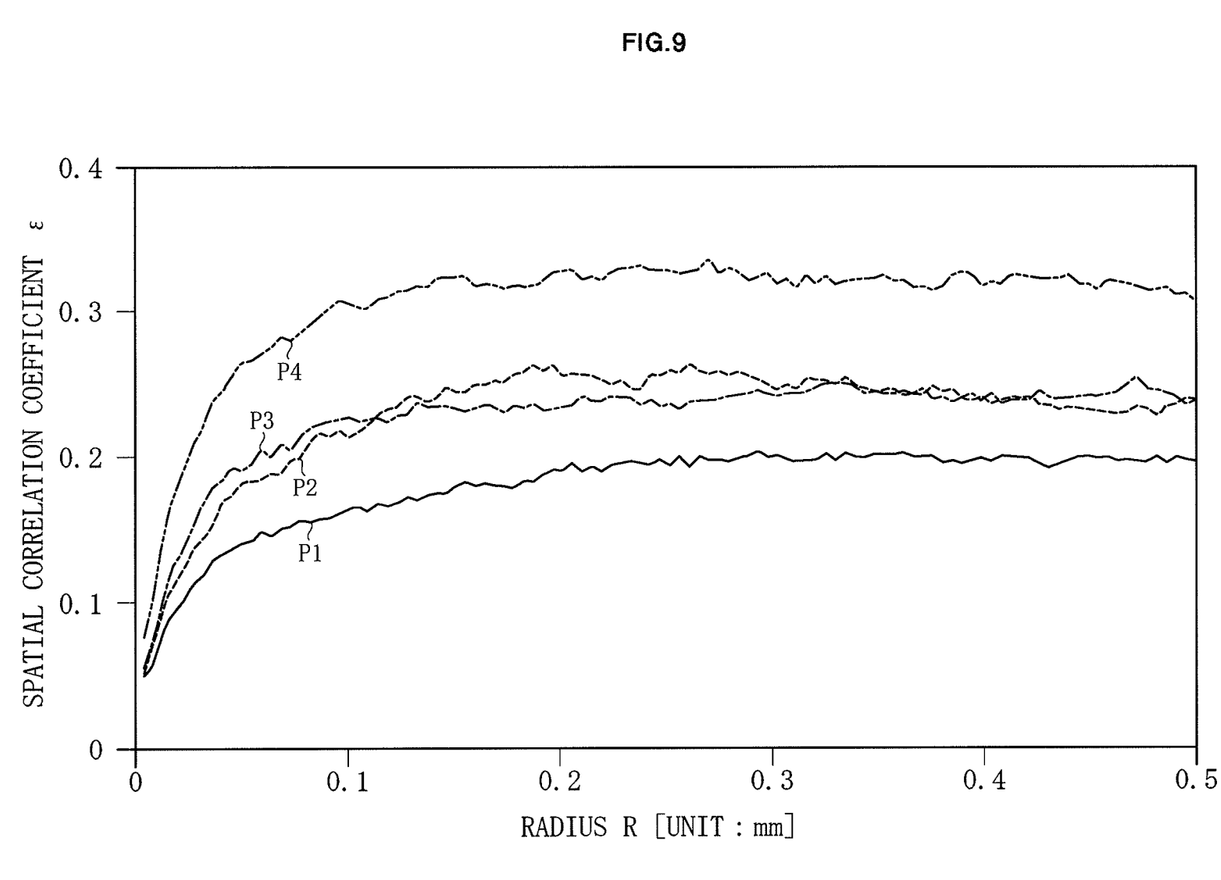
FIG. 9 is a graph of average first spatial correlation coefficients calculated in Example 5.

As shown in FIG. 9, it can be seen that the average first spatial correlation coefficients E according to the tissue sections P1 to P4 all increase like a logarithmic function when the radius R is less than 0.19 mm, and do not greatly vary when the radius R is 0.19 mm or more. When comparing the graphs at the same radius R, the average first spatial correlation coefficient E according to the tissue section P4 is larger than the average first spatial correlation coefficients ε according to the tissue sections P1 to P3. In a radius R of 0.19 mm or more, the average first spatial correlation coefficient ε according to the tissue section P4 is about 1.3 times the average first spatial correlation coefficient ε according to the tissue section P3, and in a radius R of around 0.01 mm, the slope of the graph of the average first spatial correlation coefficient according to the tissue section P4 is about 1.3 times the slope of the graph of the average first spatial correlation coefficient ε according to the tissue section P3. Therefore, from the graph of the average first spatial correlation coefficient ε, it is possible to easily discriminate the morbidity of the tissue section P3 from the morbidity of the tissue section P4. Also, it can also be seen from the graph of the average first spatial correlation coefficient ε that it is possible to easily discriminate the morbidity of the tissue section P1 from the morbidity of the tissue section P2.

Figure 10:
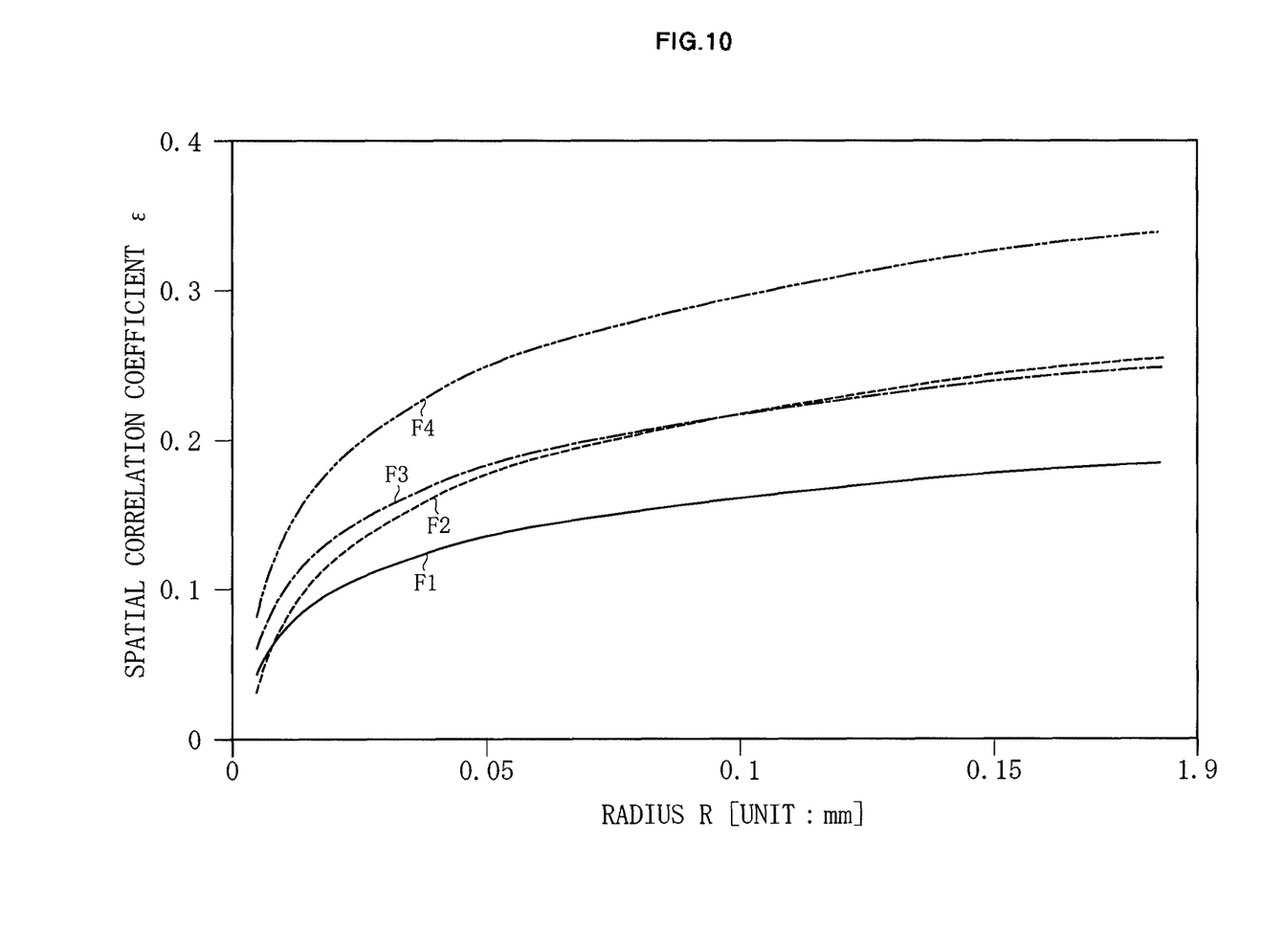
FIG. 10 is a graph of approximate expressions representing average first spatial correlation coefficients according to Example 5.

Next, the image analysis device 40 calculated approximate expressions F1 to F4 representing the average first spatial correlation coefficients ε according to the tissue sections P1 to P4. Specifically, as the approximate expressions F1 to F4 representing the average first spatial correlation coefficients ε, the image analysis device 40 calculated coefficient a, constant term b and constant α included in the approximate expressions F1 to F4 (refer to the following expression (2)), which become a polynomial including a logarithmic function when the radius R is less than 0.19 mm and become a constant when the radius R is 0.19 mm or more, as the second spatial correlation coefficients. The calculation results of the coefficient a, the constant term b, and the constant α according to each of the approximate expressions F1 to F4 are shown in the following [Table 1]. Also, graphs of the approximate expressions F1 to F4 when the radius R is less than 0.19 mm are shown in FIG. 10. As shown in FIG. 10, the graphs of the approximate expressions F1 to F4 are approximate to the graphs of the average first spatial correlation coefficients ε according to the tissue sections P1 to P4 (see FIG. 9).

[Expression 2]

$$\begin{cases} \varepsilon = a\log_e \frac{R}{b} + \alpha & (R < 0.19) \\ \varepsilon = \alpha & (0.19 \leq R) \end{cases} \quad (2)$$

TABLE 1

|  | a | b | α |
|---|---|---|---|
| approximate expression F1 | 0.0384 | 0.2549 | 0.1979 |
| approximate expression F2 | 0.0605 | 0.1586 | 0.2468 |
| approximate expression F3 | 0.0511 | 0.1583 | 0.2411 |
| approximate expression F4 | 0.0699 | 0.1452 | 0.3234 |

As shown in Table 1, it can be seen that the coefficient a of the approximate expression F4 is sufficiently larger than the coefficients a of the approximate expressions F1 to F3 and the coefficient a of the approximate expression F1 is sufficiently smaller than the coefficients a of the approximate expressions F2 to F4. Also, it can be seen that the constant term b of the approximate expression F4 is sufficiently smaller than the constant terms b of the approximate expressions F1 to F3 and the constant term b of the approximate expression F1 is sufficiently larger than the constant terms b of the approximate expressions F2 to F4. Furthermore, it can be seen that the difference between the constants α of the approximate expressions F3 and F4 is larger than the difference between the constants α of the approximate expressions F2 and F3, and the difference is remarkable. It can be seen that the difference between the constants α of the approximate expressions F1 and F2 is also larger than the difference between the constants α of the approximate expressions F2 and F3, and the difference is remarkable. Therefore, in the present example, it is possible to easily discriminate between the morbidity (cancer) of the tissue section P4 and the morbidity of the tissue section P3, and it is possible to easily discriminate between the morbidity of the tissue section P1 and the morbidity of the tissue section P2.

The present invention is not limited to the above embodiment, and the above configuration can be appropriately changed. For example, in the above example, the image analysis device 40 calculated the index of morbidity by performing any one of the above (A) to (D), but the image analysis device 40 may calculate a plurality of indices of morbidity by performing two or more of the above (A) to (D). Moreover, the method of calculating the index may be changed, as long as a highly reliable diagnosis can be supported.

Further, the configuration of the extension device 10 may be changed, as long as the tissue section P can be extended. For example, the extension device 10 may be configured to extend the stretchable sheet 60 and the tissue section P using an actuator constituted by an electric motor.

Moreover, the material for forming the stretchable sheet 60 may be changed, as long as the tissue section P can be extended. For example, the stretchable sheet 60 may be a silicone hydrogel sheet formed of silicone hydrogel.

Also, in the morbidity diagnosis support method according to the above embodiment, the tissue section P is extended by the extension device 10 in the tissue section extension step S2. However, the stretchable sheet 60 and the tissue section P may be extended by hand without using a mechanical device.

In addition, in the above example, it is configured to extend the tissue section P in one linear direction. However, the tissue section P may be extended in a plurality of linear directions. That is, for example, the stretchable sheet 60 may be stretched in two mutually orthogonal linear directions included in surface direction X of the stretchable sheet 60. In this case, the stretchable sheet 60 may be stretched simultaneously from a plurality of directions, or the direction in which the stretchable sheet 60 is stretched may be sequentially changed.

Moreover, in the above example, it is configured to analyze the image data of the stretched tissue section P. However, a configuration in which the image data obtained by image-photographing the tissue section P are analyzed may be adopted at the time of extension when the tissue section P continues to be extended, at the time of extension completion when the tissue section P is held in the state where the extension is completed, at the time of contraction of the extended tissue section P, or the like.

Further, the configuration of the output device 50 may be changed, as long as the calculated index can be outputted. For example, the output device 50 may be constituted by a printer that prints the calculated index on a paper.

Furthermore, in the above example, it is configured to support morbidity diagnosis of mice. However, the present invention is not limited to the mice and may support morbidity diagnosis of humans and non-human organisms. Also, in the above example, it is configured to support morbidity diagnosis of liver. However, the present invention is not limited to the liver and may support morbidity diagnosis of viscera other than the liver and other organs such as skin. In particular, while it is conventional pathological knowledge that intercellular adhesion is weakened in cancer tissues, it becomes possible to quantitatively evaluate the intercellular adhesion properties by using this method. Further, the present invention can be used not only for supporting morbidity diagnosis but also for grasping the state of cellular tissues of human and non-human organisms.

DESCRIPTION OF REFERENCE SIGNS

1 Morbidity diagnosis support system
1A Morbidity diagnosis data-generating system
2 Prepared slide
10 Extension device
20 Microscope
30 Image-photographing device
40 Image analysis device
50 Output device
60 Stretchable sheet
P Tissue section

The invention claimed is:

1. A morbidity diagnosis support system comprising:
an extension device for extending a tissue section of cells;
an image-photographing device for acquiring image data by image-photographing the tissue section;
an image analysis device for analyzing the image data to calculate an index of morbidity based on a mode of cracks generated in the tissue section by the extension; and
an output device for outputting the calculated index.

2. The morbidity diagnosis support system according to claim 1, wherein the extension device extends the tissue section by clipping a stretchable sheet provided with the tissue section and stretching the stretchable sheet.

3. The morbidity diagnosis support system according to claim 2, wherein the stretchable sheet is formed of polyurethane gel.

4. The morbidity diagnosis support system according to claim 1, wherein the image analysis device calculates an area of cells contained in the tissue section and an area of cracked part generated in the tissue section, and calculates the index based on the area of cells and the area of cracked part.

5. The morbidity diagnosis support system according to claim 1, wherein the image analysis device calculates an area of cracked part generated in the tissue section and a length of the cracked part, and calculates the index based on the area and length of cracked part.

6. The morbidity diagnosis support system according to claim 1, wherein the image analysis device converts at least a part of an image photographed by the image-photographing device into a spatial frequency domain, and calculates the index based on a frequency distribution obtained as a result of conversion into the spatial frequency domain.

7. The morbidity diagnosis support system according to claim 1, wherein the image analysis device calculates a spatial correlation coefficient representing a feature of a geometric shape of a crack based on a shape of the crack on an image photographed by the image-photographing device, and calculates the index based on the spatial correlation coefficient.

8. A morbidity diagnosis support method comprising:
   a tissue section extension step of extending a tissue section of cells;
   an image data acquisition step of acquiring image data of the tissue section by an image-photographing device;
   an index calculation step of calculating an index of morbidity based on a mode of cracks generated in the tissue section by the extension, by allowing an image analysis device to analyze the image data; and
   an index output step of outputting the index by an output device.

9. The morbidity diagnosis support method according to claim 8, further comprising a prepared slide creation step of creating a prepared slide by providing the tissue section on a stretchable sheet, wherein the tissue section is extended by stretching the stretchable sheet in the tissue section extension step.

10. The morbidity diagnosis support method according to claim 9, wherein the tissue section is stained in the prepared slide creation step.

11. The morbidity diagnosis support method according to claim 9, wherein a polyurethane gel sheet is used as the stretchable sheet in the prepared slide creation step.

\* \* \* \* \*